(12) United States Patent
      Qu et al.

(10) Patent No.: US 12,558,185 B2
(45) Date of Patent: Feb. 24, 2026

(54) GUIDING AND POSITIONING DEVICE FOR ASSISTING IN COMPUTED TOMOGRAPHY-GUIDED NEEDLE BIOPSY (CT-GNB)

(71) Applicant: READITEC MEDICAL SYSTEMS CO., LTD., Zhuhai (CN)

(72) Inventors: Feihuan Qu, Chengdu (CN); Feng Shou, Xi'an (CN); Fujun Zhang, Guangzhou (CN); Chuang He, Guangan (CN); Shifu Ye, Jianyang (CN); Lei Ma, Chengdu (CN); Taojin Huang, Chengdu (CN); Qingchun Zhou, Chengdu (CN); Zhisheng Wu, Chongqing (CN); Guangyue Shi, Chengdu (CN); Xi Jia, Chengdu (CN)

(73) Assignee: READITEC MEDICAL SYSTEMS CO., LTD., Zhuhai (CN)

( * ) Notice: Subject to any disclaimer, the term of this patent is extended or adjusted under 35 U.S.C. 154(b) by 230 days.

(21) Appl. No.: 18/550,293

(22) PCT Filed: Dec. 6, 2021

(86) PCT No.: PCT/CN2021/135686
      § 371 (c)(1),
      (2) Date: Sep. 13, 2023

(87) PCT Pub. No.: WO2022/199123
      PCT Pub. Date: Sep. 29, 2022

(65) Prior Publication Data
      US 2024/0268917 A1     Aug. 15, 2024

(30) Foreign Application Priority Data
      Mar. 24, 2021    (CN) .......................... 202110311522.3

(51) Int. Cl.
      *A61B 90/11*      (2016.01)
      *A61B 17/34*      (2006.01)
      *A61B 90/00*      (2016.01)

(52) U.S. Cl.
      CPC .......... *A61B 90/11* (2016.02); *A61B 17/3403* (2013.01); *A61B 90/37* (2016.02);
      (Continued)

(58) Field of Classification Search
      CPC ........ A61B 17/3403; A61B 2017/3405; A61B 2017/3407; A61B 90/10; A61B 90/11; A61B 2090/101
      See application file for complete search history.

(56) References Cited

U.S. PATENT DOCUMENTS

| | | | |
|---|---|---|---|
| 2002/0007188 A1* | 1/2002 | Arambula | .......... A61B 17/1757 |
| | | | 606/130 |
| 2015/0230871 A1* | 8/2015 | Sayler | .................... A61B 90/14 |
| | | | 128/845 |

(Continued)

FOREIGN PATENT DOCUMENTS

| | | |
|---|---|---|
| CN | 201595839 U | 10/2010 |
| CN | 208524983 U | 2/2019 |

(Continued)

*Primary Examiner* — Martin T Ton
(74) *Attorney, Agent, or Firm* — Bayramoglu Law Offices LLC

(57) ABSTRACT

A guiding and positioning device for assisting in computed tomography-guided needle biopsy (CT-GNB) includes a control mechanism and an actuating mechanism, where the actuating mechanism includes a base and a support frame; one of the two head ends of the support frame is provided with a locking mechanism; a positioning apparatus includes a first guide rail in an arc shape, and the first guide rail is slidably provided with a guiding apparatus configured to guide different puncture angles in a same plane; the guiding apparatus includes a deflection drive mechanism slidable (Continued)

along the first guide rail, and a first translation mechanism and a second translation mechanism that are arranged perpendicular to each other; and the second translation mechanism is slidably provided with a guiding mechanism configured to guide a puncture through a visible laser space.

11 Claims, 13 Drawing Sheets

(52) U.S. Cl.
      CPC ................. *A61B 2017/3407* (2013.01); *A61B 2090/3762* (2016.02)

(56)                        References Cited

U.S. PATENT DOCUMENTS

| | | | |
|---|---|---|---|
| 2017/0333724 | A1 | 11/2017 | Lee et al. |
| 2018/0110571 | A1* | 4/2018 | Hallen ................... A61B 34/37 |
| 2018/0132951 | A1* | 5/2018 | Olson ................... A61B 90/50 |
| 2018/0279992 | A1* | 10/2018 | Frankel ................ A61G 13/101 |
| 2020/0107890 | A1* | 4/2020 | Hashimoto ........... B25J 9/1689 |
| 2021/0369388 | A1* | 12/2021 | Chauhan ................ A61B 34/37 |

FOREIGN PATENT DOCUMENTS

| | | | | |
|---|---|---|---|---|
| CN | 109431610 | A * | 3/2019 | ............ A61B 34/30 |
| CN | 109984825 | A | 7/2019 | |
| CN | 111000623 | A | 4/2020 | |
| CN | 211433207 | U | 9/2020 | |
| CN | 112690881 | A | 4/2021 | |
| WO | 2009042130 | A2 | 4/2009 | |
| WO | 2015057807 | A1 | 4/2015 | |

* cited by examiner

GUIDING AND POSITIONING DEVICE FOR ASSISTING IN COMPUTED TOMOGRAPHY-GUIDED NEEDLE BIOPSY (CT-GNB)

CROSS REFERENCE TO THE RELATED APPLICATIONS

This application is the national phase entry of International Application No. PCT/CN2021/135686, filed on Dec. 6, 2021, which is based upon and claims priority to Chinese Patent Application No. 202110311522.3, filed on Mar. 24, 2021, the entire contents of which are incorporated herein by reference.

TECHNICAL FIELD

The present disclosure belongs to the technical field of medical devices, and in particular, the present disclosure relates to a surgical medical device and specifically to a guiding and positioning device for assisting in computed tomography-guided needle biopsy (CT-GNB).

BACKGROUND

Needle biopsy is the main method for histopathological diagnosis of bone and solid carcinoma. Bone and solid carcinoma are diseases that heavily endanger human health and life. In recent years, the incidence of bone and solid carcinoma has gradually increased, and the onset age of bone and solid carcinoma has gradually decreased. The early detection, accurate diagnosis, and timely treatment of bone and solid carcinoma has an important impact on prognosis. With the continuous improvement of examination means and methods, the accuracy rate of diagnosis of bone and solid carcinoma has gradually improved, but there are still a large number of tumors that do not have typical imaging characteristics and cannot easily be diagnosed. The accurate diagnosis of these tumors requires the combination of clinical diagnosis, imaging diagnosis, and pathological diagnosis, where the pathological diagnosis plays a key role in the selection of a treatment plan. Needle biopsy is a main way for pathological diagnosis. However, the formulation of a biopsy plan should be highly valued like the formulation of a surgery plan because a biopsy is a crucial first step of tumor treatment, and an inaccurate biopsy may bring disastrous consequences for a patient. The accuracy of the puncture is the key for a biopsy. It is most common in the prior art that an image of an affected part of a patient is acquired through computed tomography (CT), positron emission tomography-computed tomography (PET-CT), magnetic resonance imaging (MRI), or the like and then a puncture site and direction is determined based on the image to collect the target tissue. Since the accuracy of the puncture plays a crucial role in needle biopsy, the puncture point and angle are the most important. For special parts, such as areas densely covered with bone substances, blood vessels, and organs, it is extremely difficult to allow a puncture, which poses a great challenge for an accurate puncture.

A variety of minimally-invasive treatments such as microwave ablation (MWA), radio frequency ablation (RFA), and particle implantation can also be conducted through the puncture. Puncture treatments have characteristics such as small traumas, fast recovery, and excellent therapeutic effects, and have been widely conducted by increasing medical institutions in recent years. However, these minimally-invasive treatments require an operator to accurately puncture to deliver a therapeutic action source to a specific tumor site, which has high accuracy requirements. An inaccurate puncture may lead to incomplete ablation of the target tumor to seriously affect the efficacy, and may also lead to intraoperative risks such as accidental penetration through a blood vessel and damage to an organ by the puncture needle.

Therefore, in order to improve the accuracy of puncture for a biopsy and a minimally-invasive treatment, a device capable of reducing or even eliminating the puncture deviation is required to avoid or even eliminate an accident caused by multiple punctures or a puncture deviation.

SUMMARY

The existing puncture technique faces various problems caused by inaccurate punctures due to the absence of an accurate auxiliary device, and may cause serious consequences such as pneumothorax, critical conditions, and death in severe cases. In order to reduce or even eliminate many problems caused by a low puncture accuracy and avoid a secondary damage to a patient, the present disclosure provides a guiding and positioning device for assisting in CT-GNB to allow guiding and positioning for a puncture. Specifically, the device of the present disclosure can accurately guide the determination of an accurate puncture needle channel based on an image obtained through CT scanning to avoid a puncture deviation of a doctor during a puncture operation due to the absence of a puncture angle.

In order to allow the above objective, the present disclosure particularly provides a guiding and positioning device for assisting in CT-GNB, including: a control mechanism and an actuating mechanism, where the actuating mechanism includes a base and a support frame arranged on the base to support a positioning apparatus; the support frame has two head ends rotatably connected to the positioning apparatus, and one of the two head ends of the support frame is provided with a locking mechanism configured to limit a deflection angle of the positioning apparatus; the positioning apparatus includes a first guide rail in an arc shape, and the first guide rail is slidably provided with a guiding apparatus configured to guide a spatial puncture angle; the guiding apparatus includes a deflection drive mechanism slidable along the first guide rail, and a first translation mechanism and a second translation mechanism that are arranged perpendicular to each other; and the second translation mechanism is slidably provided with a guiding mechanism configured to guide a puncture through a visible laser space.

As one of the detailed solutions of the present disclosure, preferably, the deflection drive mechanism includes a guide frame as a support body, a second servo motor removably and fixedly arranged on the guide frame, a driving wheel connected to the second servo motor and drivably connected to the first guide rail, and a plurality of stabilizing wheels rotatably arranged on the guide frame and located at inner and outer sides of the first guide rail.

As one of the detailed solutions of the present disclosure, preferably, the first translation mechanism includes a second guide rail removably and fixedly arranged on the guide frame, a slide seat slidably clamped on the second guide rail, a third servo motor drivably connected to two ends of the second guide rail through a belt, and a follower; and the slide seat is removably and fixedly connected to the belt.

Further preferably, the second translation mechanism includes an L-shaped bracket fixedly connected to the slide seat; the L-shaped bracket is removably connected to a slide rail arranged perpendicular to the second guide rail, and an end of the slide rail is provided with a fourth servo motor;

the fourth servo motor drives the guiding mechanism to reciprocate along the slide rail through a screw; and the guiding mechanism includes one or more laser transmitters arranged along a same straight line.

Preferably, the positioning apparatus further includes a support arm that has one end removably and fixedly connected to the first guide rail and the other end rotatably connected to a head end of the support frame; and an end of the support arm away from the first guide rail is connected to the locking mechanism.

As a structural design of a manual locking mechanism, preferably, the locking mechanism includes: a handle fixedly connected to the support arm, where a locking pin penetrates through the handle; and a locking plate fixedly arranged on the support frame and configured to cooperate with the locking pin to lock the support arm, where the locking plate is provided with a plurality of adjacent blind holes configured to accommodate the locking pin.

As a structural design of a high-accuracy automatic locking mechanism, preferably, the locking mechanism includes a reversing reducer drivably connected to the support arm and a first servo motor drivably connected to the reversing reducer.

Preferably, the control mechanism includes the following units configured to acquire execution parameters: an input unit, including an ergonomic input module configured to acquire parameter information and/or a data analysis module configured to read imported message data;

a processing unit configured to allocate parameter information acquired by the input unit to a corresponding decoding module according to a preset control logic of a system, where the decoding module is configured to convert the parameter information into a corresponding driving signal; and an actuating unit configured to send a driving signal to the actuating mechanism according to a preset driving logic.

Preferably, the base is removably and fixedly connected to the support frame through a connector; an adjustment mechanism in threaded connection with the support frame is horizontally provided on the base; and the adjustment mechanism includes a first adjustment screw and a second adjustment screw, and projection lines of straight lines presented by the first adjustment screw and the second adjustment screw in a horizontal direction are perpendicular to each other.

In order to be compatible with a practical application scenario and a cost, preferably, a central angle corresponding to the first guide rail is 180° to 360°. The larger the central angle of the first guide rail, the wider the available puncture range; and when the central angle of the first guide rail reaches 360°, a dead space-free puncture can be allowed for a radial end face of a patient.

Beneficial Effects

1. The guiding and positioning device of the present disclosure can be used in combination with the existing imaging device, such as a CT device and a PET-CT device. With puncture needle channel information determined according to an image acquired by an imaging device such as a CT machine, the guiding and positioning device can accurately guide in a space to assist in an operation of a doctor, thereby avoiding deviations and errors in experience-based manual punctures.

2. The present disclosure can allow a deflection in a radial plane and a head-foot direction of a patient, can guide a puncture in areas densely covered with blood vessels, organs, and bone substances, and has a wide range of applications.

BRIEF DESCRIPTION OF THE DRAWINGS

To describe the technical solutions in the embodiments of the present disclosure or in the prior art more clearly, the accompanying drawings required for describing the embodiments or the prior art are briefly described below. Apparently, the accompanying drawings in the following description merely show some embodiments of the present disclosure, and a person of skill in the art may still derive other accompanying drawings from these accompanying drawings without creative efforts.

Figure 1:
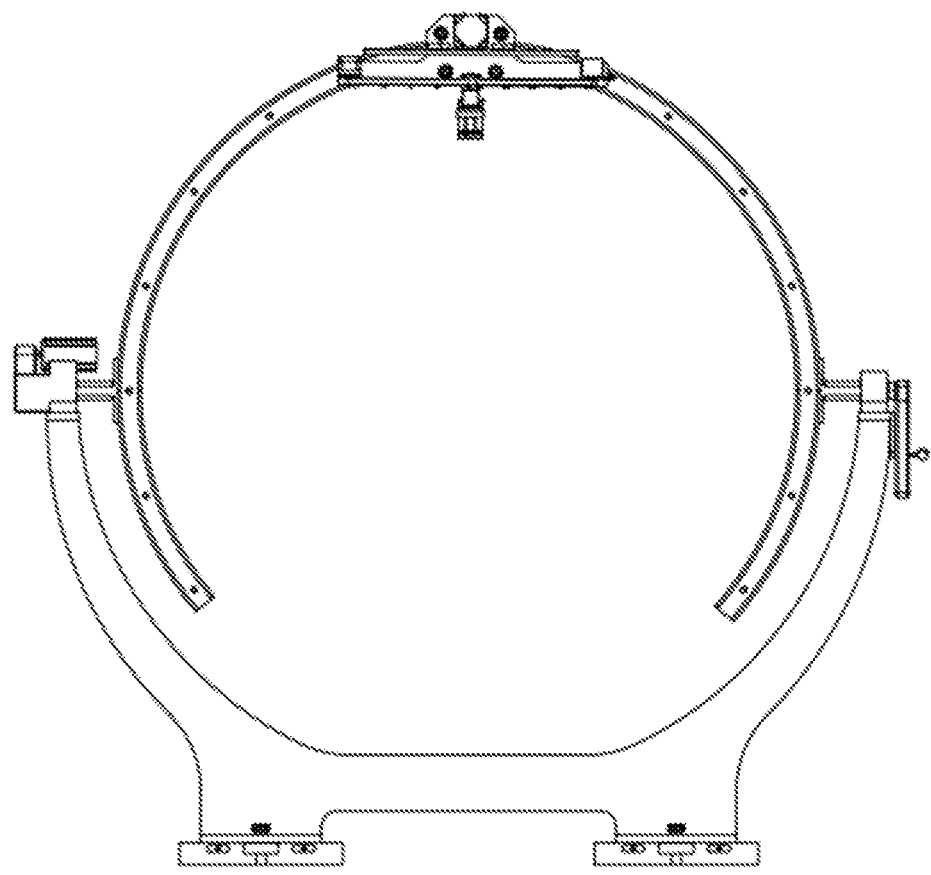
FIG. 1 is a front view of a first guide rail designed at 270° in the present disclosure.
Figure 2:
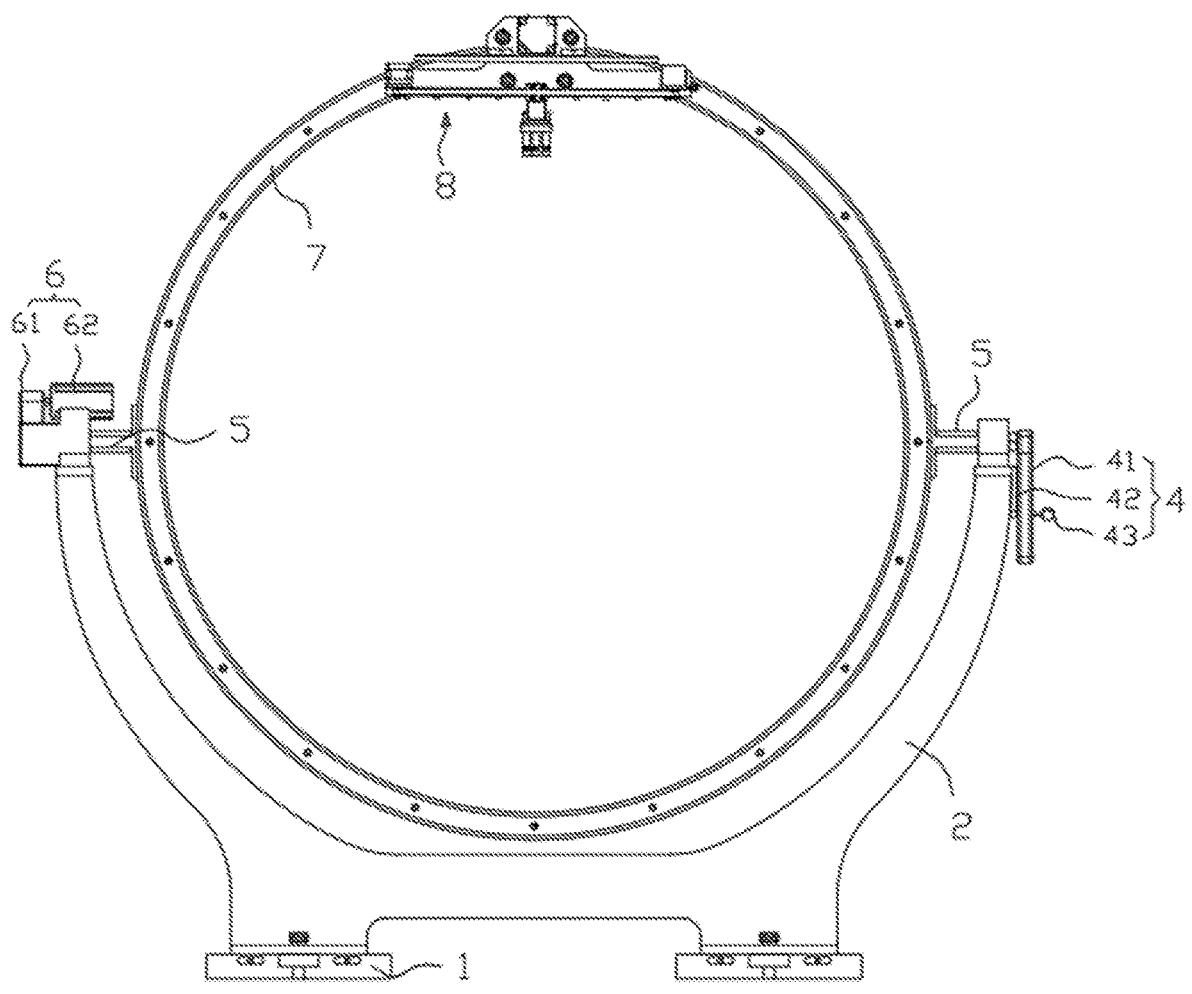
FIG. 2 is a front view of a first guide rail designed at 360° in the present disclosure.
Figure 3:
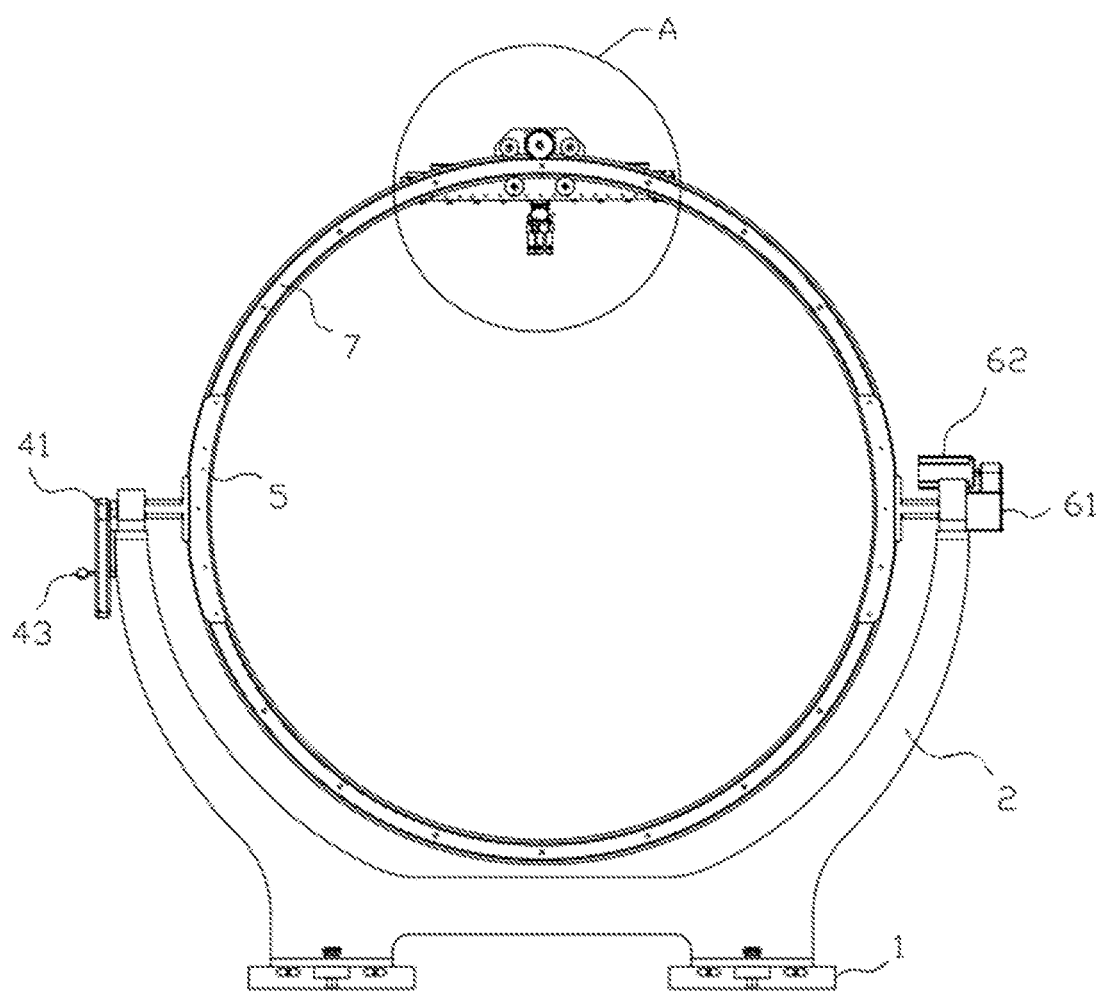
FIG. 3 is a rear view of FIG. 2.

Reference numerals: 1: base; 2: support frame; 3: leveling instrument; 4: locking mechanism; 41: handle; 42: locking plate; 43: locking pin; 5: support arm; 6: deflection driver; 61: reversing reducer; 62: first servo motor; 7: first guide rail; 8: guiding apparatus; 81: second servo motor; 82: guide frame; 83: driving wheel; 84: stabilizing wheel; 85: second guide rail; 86: third servo motor; 87: first translation mechanism; 871: belt; 872: slide seat; 873: follower; 88: second translation mechanism; 881: slide rail; 882: L-shaped bracket; and 89: guiding mechanism.

DETAILED DESCRIPTION OF THE EMBODIMENTS

In order to make the objectives, technical solutions, and advantages of the embodiments of the present disclosure clear, the technical solutions in the embodiments of the present disclosure are clearly and completely described below with reference to the accompanying drawings in the embodiments of the present disclosure. Apparently, the described embodiments are some rather than all of the embodiments of the present disclosure. Generally, components of the embodiments of the present disclosure described and shown in the accompanying drawings may be arranged and designed in various manners.

Therefore, the following detailed description of the embodiments of the present disclosure in the accompanying drawings is not intended to limit the protection scope of the present disclosure, but merely indicates selected embodiments of the present disclosure. All other embodiments obtained by a person of ordinary skill in the art based on the embodiments of the present disclosure without creative efforts shall fall within the protection scope of the present disclosure.

It should be noted that similar reference signs and letters represent similar items in the accompanying drawings below. Therefore, once an item is defined in one accompanying drawing, it does not need to be further defined and described in subsequent accompanying drawings.

In the description of the present disclosure, it should be noted that orientation or position relationships indicated by terms such as "center", "upper", "lower", "left", "right", "vertical", "horizontal", "inner", and "outer" are orientation or position relationships shown in the accompanying drawings or when the product of the present disclosure is usually placed in operation. These terms are only used to facilitate description of the present disclosure and simplify the description, rather than to indicate or imply that the mentioned apparatus or components must have a specific orientation or must be established and operated in a specific orientation, and thus these terms cannot be construed as a limitation to the present disclosure. In addition, in the description of the present disclosure, terms such as "first" and "second" are used only for distinguishing and cannot be understood as indicating or implying relative importance.

Moreover, terms such as "horizontal" and "vertical" in the description of the present disclosure do not require a corresponding component to be absolutely horizontal or overhanging, but the component can be tilted slightly. If "horizontal" only means that a direction of the component is more horizontal than "vertical", it does not mean that the structure must be completely horizontal, but can be tilted slightly.

In the description of the present disclosure, it should be noted that, unless otherwise clearly specified, meanings of terms "arrange", "connected with", and "connected to" should be understood in a broad sense. For example, the connection may be a fixed connection, a removable connection, or an integral connection; may be a mechanical connection or an electrical connection; may be a direct connection or an indirect connection through an intermediate medium; or may be intercommunication between two components. Those of ordinary skill in the art may understand the specific meanings of the above terms in the present disclosure based on specific situations.

Embodiment 1

Figure 11:
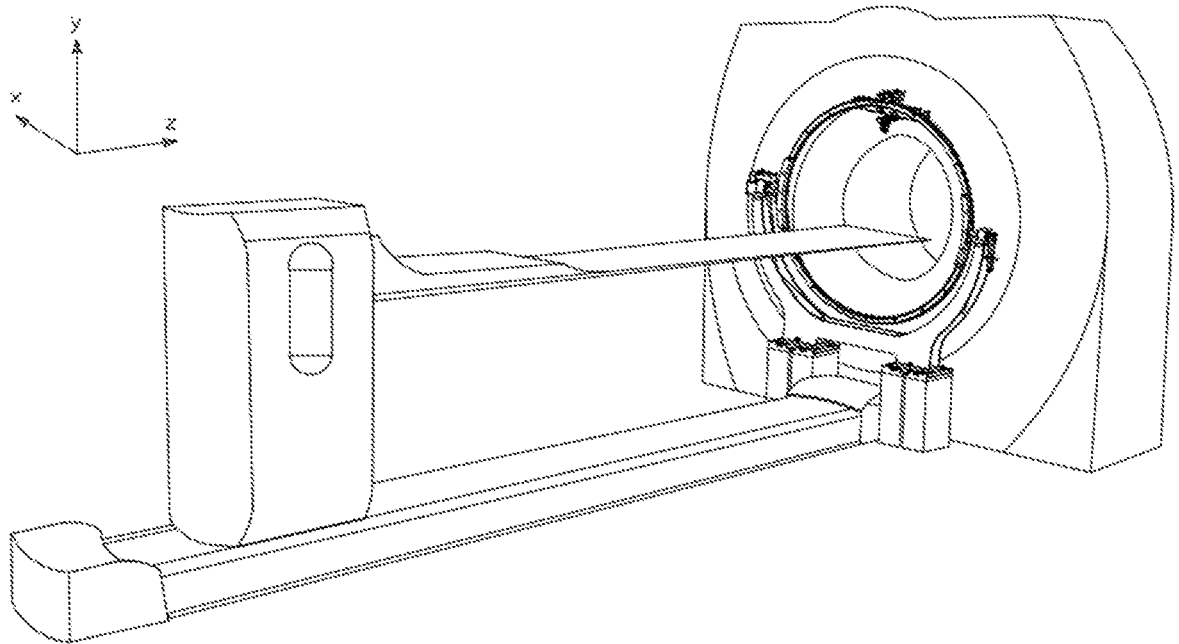
FIG. 11 is a schematic diagram of a status of the present disclosure when used in combination with a CT machine.

This embodiment is intended to describe a process and principle of assisting in a guided puncture and a structure involved in conjunction with the existing CT machine. Specifically, as shown in FIG. 1 to FIG. 4, this embodiment provides a guiding and positioning device for assisting in CT-GNB, including: a control mechanism and an actuating mechanism, where the actuating mechanism includes base 1 and support frame 2 arranged on the base 1 to support a positioning apparatus; the support frame 2 has two head ends rotatably connected to the positioning apparatus, and one of the two head ends of the support frame (2) is provided with locking mechanism 4 configured to limit a deflection angle of the positioning apparatus; the positioning apparatus includes first guide rail 7 in an arc shape, and the first guide rail 7 is slidably provided with guiding apparatus 8 configured to guide a spatial puncture angle; the guiding apparatus 8 includes a deflection drive mechanism slidable along the first guide rail 7, and first translation mechanism 87 and second translation mechanism 88 that are arranged perpendicular to each other; and the second translation mechanism 88 is slidably provided with guiding mechanism 89 configured to guide a puncture through a visible laser space. The arrangement, operation, and principle for the guided puncture in this embodiment are as follows:

As shown in FIG. 11, the guiding and positioning device provided in this embodiment is arranged coaxially with a detection cavity of a CT machine, and the guiding and positioning device is located in front of the CT machine. Since the existing CT machine beds all have a high-accuracy movement function, in a case that a movement range of the CT machine is allowed, it is also possible to coaxially arrange the guiding and positioning device provided in this embodiment behind the CT machine. The guiding and positioning device provided in this embodiment can be arranged coaxially with the CT machine to allow guidance, and a specific principle of the guidance is as follows:

After the arrangement is completed, a patient is allowed to lie flat or lie on a side on a CT bed, which can be conducted according to daily CT detection; and there are no other special requirements as long as it is convenient for detection and posture maintenance.

Then an affected part of the patient that needs to undergo CT detection is pasted in a head-foot direction to image parallel guidewires, and a guidewire coverage range should exceed a range to be detected to avoid a case where a CT image of a target area does not include an image of guidewires, which is not conducive to subsequent positioning.

Then the CT machine is initialized and allowed to perform a CT task, and a direction of a puncture needle channel is determined according to a CT image acquired. Because the guidewires are pasted on a body surface of the patient, a deflection angle between a preset puncture needle channel and a vertical direction and intersection points between the preset puncture needle channel and the guidewires on the body surface can be determined according to the CT image, thereby determining an actual puncture point and direction on the body surface of the patient. The puncture point can be determined in a head-foot direction of the patient through an inherent mobile positioning function of the CT bed, namely, through a number of layers and a layer thickness for the CT image; and a radial circumferential deflection distance is determined according to an intersection point between a guidewire image on the CT image and the preset puncture needle channel. If the preset puncture needle channel is between the 21st and 22nd guidewire imaging points from left to right on the image, then a radial position can be determined between the 21st and 22nd guidewires attached to the body surface of the patient; and accordingly, an intersection point between a radial direction and the head-foot direction is determined as the puncture point of the preset puncture needle channel on the body surface of the patient.

Finally, annotation information of an X-ray image for a planned puncture needle channel of the CT machine is read to determine a number of layers for the X-ray image as a basis for determining the puncture, that is, a movement distance of the CT bed when the CT machine is initialized. Since the guiding and positioning device provided in this embodiment is arranged coaxially with the CT machine, a scanning center is allowed to coincide with a center of the guiding and positioning device during initialization of the CT machine by moving the CT bed. Then a deflection angle of the preset puncture needle channel is input into the control mechanism, such that the guiding mechanism 89 is deflected along the first guide rail 7 to an angle of the preset puncture needle channel. If an indicator laser of the guiding mechanism 89 coincides with the puncture point, a guiding and positioning purpose of the guiding and positioning device is completed. If an indicator laser of the guiding mechanism does not coincide with the puncture point, it means that the preset puncture needle channel and a ray indicated by the laser are parallel to each other and a translation is required in a radial plane, namely, a plane in which the CT scanning is conducted, which is the X-Y plane in FIG. 12. In this case, a translation distance between the preset puncture needle channel and a ray that passes through a center and is parallel to the preset puncture needle channel can be read on the X-ray image by the CT machine, and then the distance parameter is input into the control mechanism to drive the first translation mechanism 87 to perform a translation action until an indicator laser of the guiding mechanism 89 coincides with the puncture point. If a parallel puncture needs to be conducted in a head-foot direction, namely, a movement direction of the CT bed, a translation is conducted by the second translation mechanism 88, and a translation distance can be a movement distance preset through an input, where a translation principle is the same as the translation principle of the first translation mechanism 87.

In this embodiment, the control mechanism is an existing servo control system, such as a communication-controlled upper computer system or an operation control system established by a PC.

Beneficial Effects

1. In this embodiment, after the guiding and positioning device is arranged, a doctor can make full use of accurate measurement and movement functions of the CT machine and a guiding and positioning function of the guiding and positioning device to allow a complete guided puncture, which greatly eliminates the influence of a large number of human factors, experience factors, and luck factors in the existing manual punctures, reduces the possibility of puncture failure, and greatly reduces or even eliminates the damage caused by a puncture to a patient. The guiding and positioning device can also be connected to a special software system to allow the continuous guidance of a complicated puncture plan, thereby reducing a work intensity of a doctor and improving the surgical safety.

2. When the guiding and positioning device provided in this embodiment is arranged in connection with a CT machine or like, a positioning accuracy can be ensured to a maximum extent, and a puncture can be conducted immediately after a CT examination of a patient, which greatly ensures the consistency of a posture of the patient, and avoids an inaccurate puncture resulting from a position or volume change of a target area caused by a postural change of the patient.

3. The guiding and positioning device provided in this embodiment has extremely-high compatibility, and can be used in combination with an existing CT machine almost of any model, which allows a hospital to acquire excellent technical effects and practical significance in the field of biopsy puncture with a relatively-low cost input.

Embodiment 2

Figure 4:
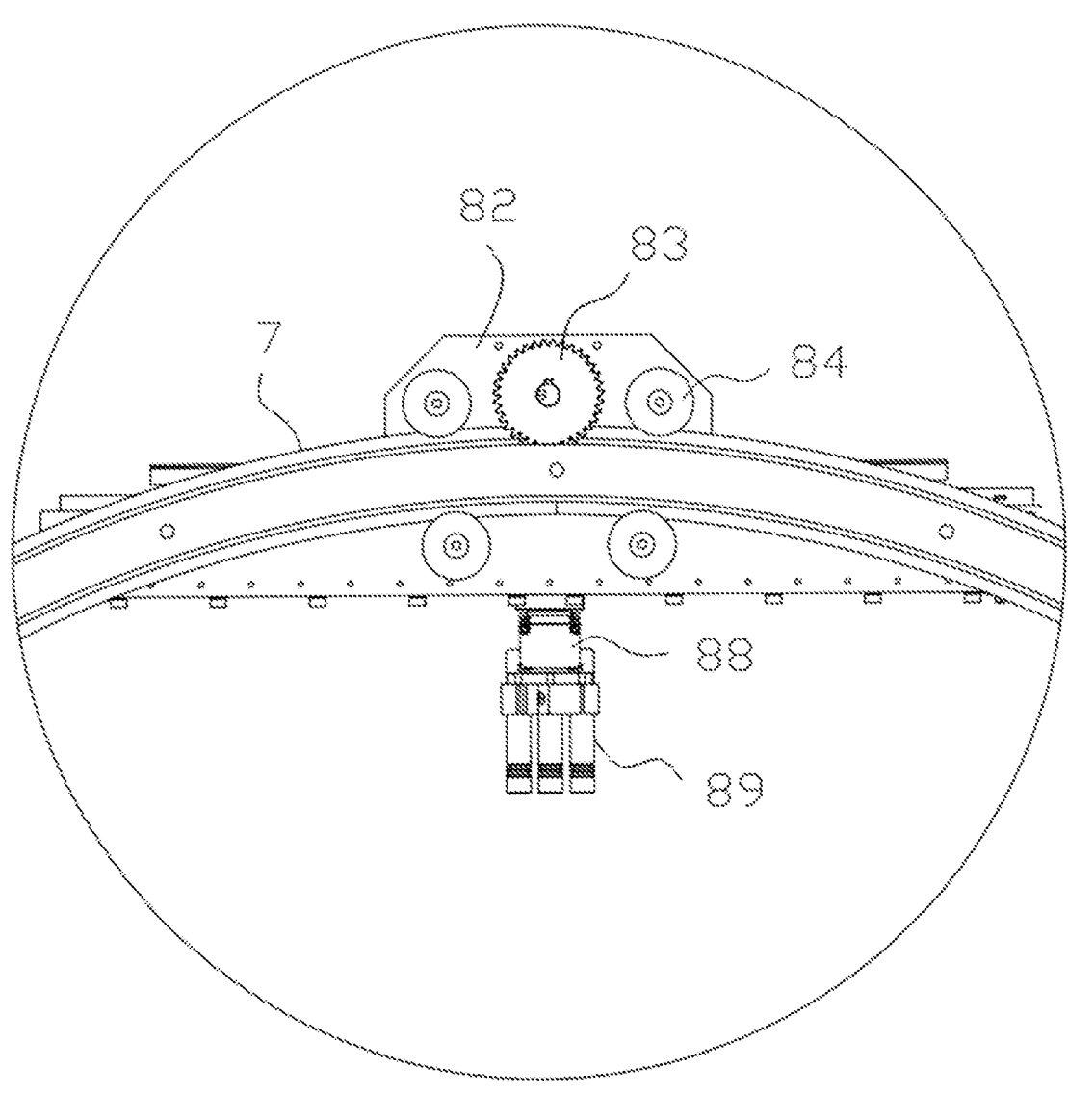
FIG. 4 is an enlarged view of A in FIG. 3.
Figure 5:
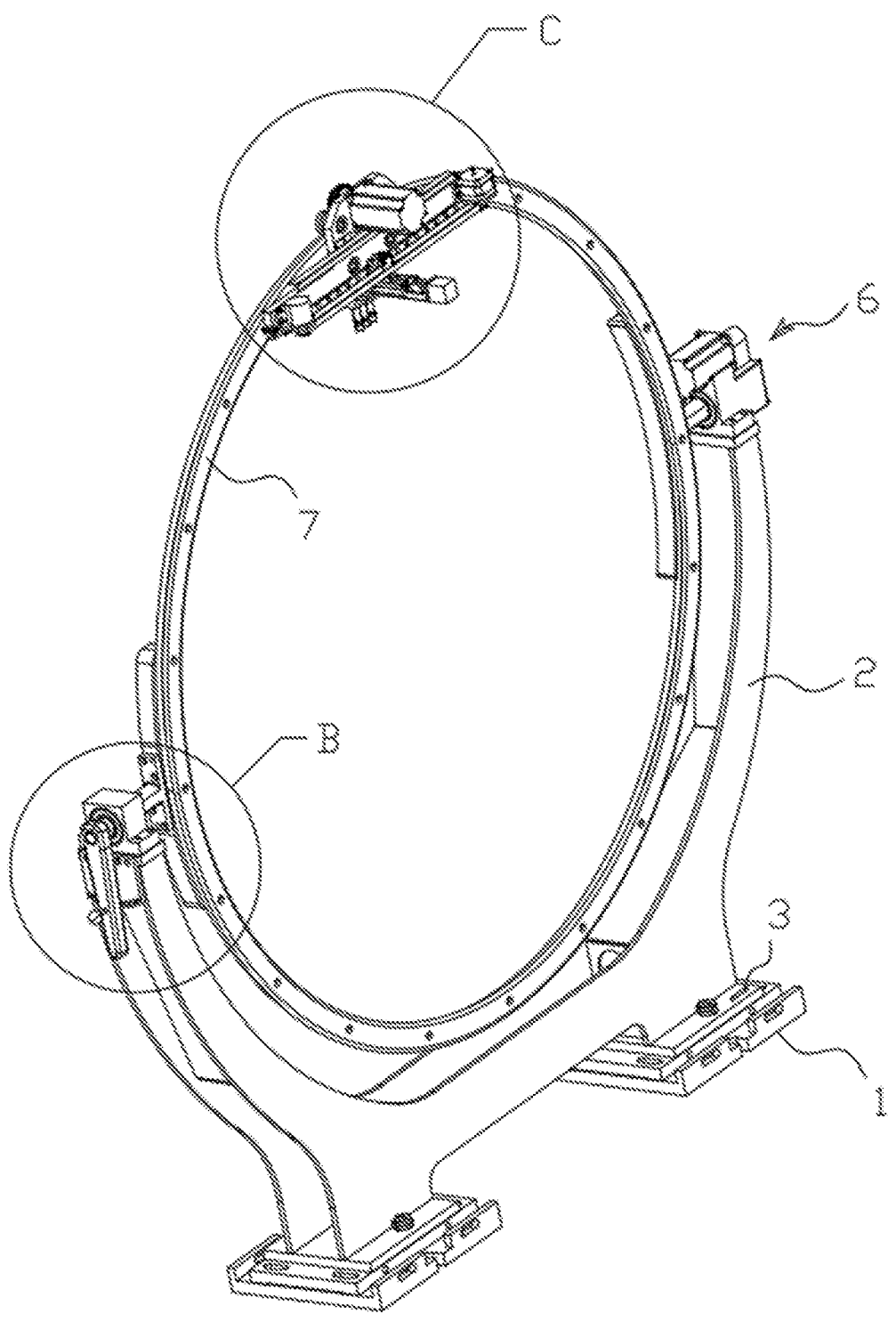
FIG. 5 is an axonometric view of FIG. 2.
Figure 6:
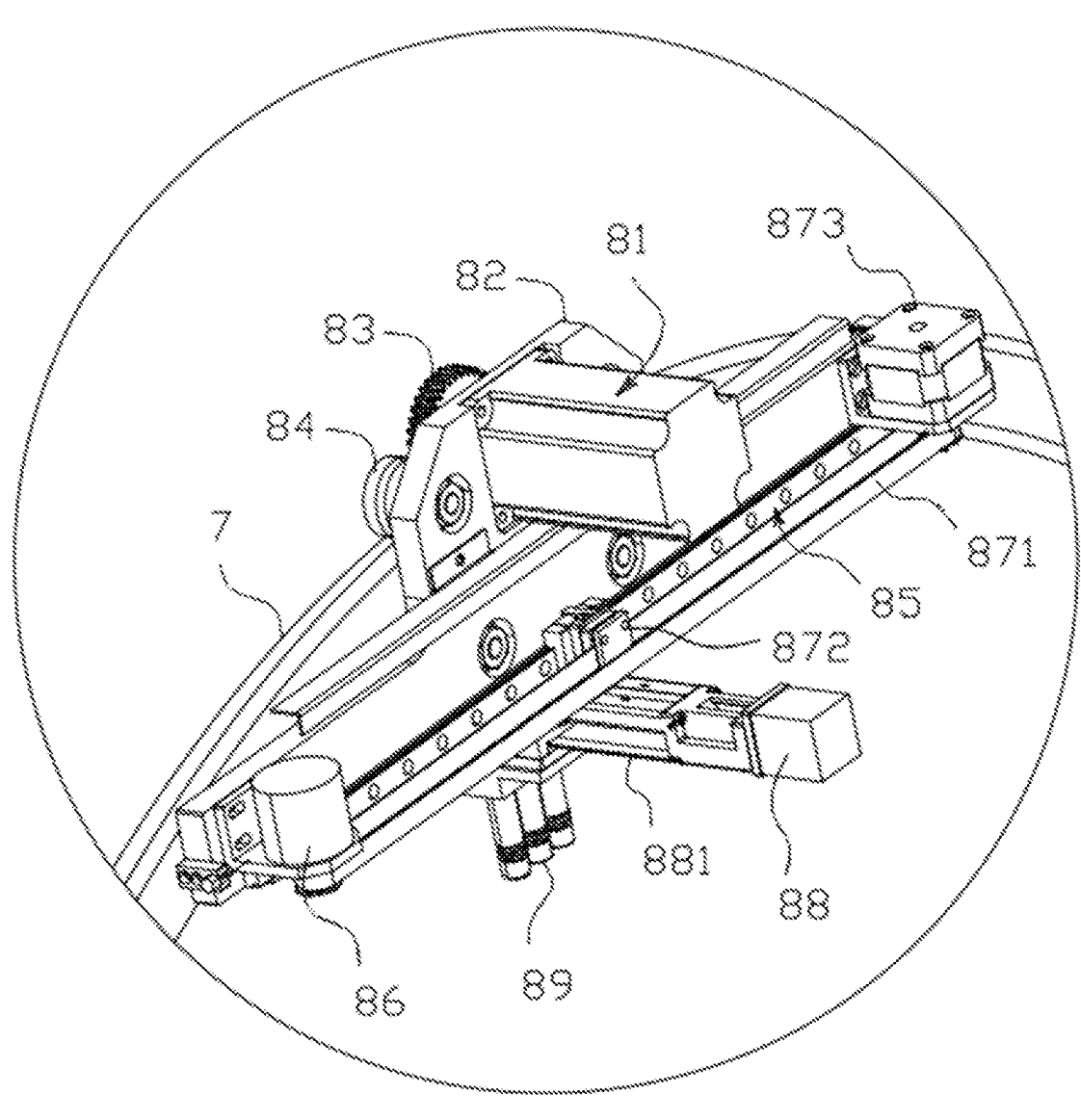
FIG. 6 is an enlarged view of B in FIG. 5.

As one of the detailed solutions of the present disclosure, Embodiment 1 is further detailed in this embodiment. As shown in FIG. 4 to FIG. 6, the deflection drive mechanism includes guide frame 82 as a support body, second servo motor 81 removably and fixedly arranged on the guide frame 82, driving wheel 83 connected to the second servo motor 81 and drivably connected to the first guide rail 7, and a plurality of stabilizing wheels 84 rotatably arranged on the guide frame 82 and located at inner and outer sides of the first guide rail 7. When a deflection needs to be conducted in a radial plane, namely, a plane in which CT scanning is conducted, the second servo motor 81 drives the driving wheel 83 in centrifugal fixed connection with the second servo motor 81 to rotate. Because the guide frame 82 is slidably connected to the first guide rail 7, under the driving of the second servo motor 81, the entire guide frame 82 moves along the first guide rail 7, where a distance of the movement determines a deflection angle, and the distance of the movement is determined by a driving signal acquired by the second servo motor 81. Because the servo motor has an extremely-high execution accuracy, a deflection accuracy can be effectively guaranteed. As shown in FIG. 4, inner and outer sides of the first guide rail 7 each are provided with stabilizing wheels 84 in pairs configured to tightly hold the first guide rail 7, which can prevent the guide frame 82 from trembling or shaking on the first guide rail 7 to affect an accuracy of a positioning indicator. The arrangement of the stabilizing wheels 84 of the present disclosure has less resistance, longer service life, and higher wear resistance than the arrangement of a slide structure to allow stability. The driving wheel 83 is implemented by a spur gear or helical gear structure, and a fine gear structure is preferred to reduce or avoid a clearance error of gear meshing as much as possible.

Embodiment 3

In this embodiment, an optimized structure is proposed based on Embodiment 2 for when a parallel puncture needs to be conducted in a plane in which the patient scanning fault is located. Specifically, as shown in FIG. 6, the first translation mechanism 87 includes second guide rail 85 removably and fixedly arranged on the guide frame 82, slide seat 872 slidably clamped on the second guide rail 85, third servo motor 86 drivably connected to two ends of the second guide rail 85 through belt 871, and follower 873; and the slide seat 872 is removably and fixedly connected to the belt 871. When an adjustment is required, the first translation mechanism 87 changes the guidance of the guiding mechanism 89 from a ray pointing to a coaxial center of the CT machine and the guiding and positioning device to a straight line at which a preset puncture needle channel is located according to parameters required for a translation measured by a CT machine, such as to allow the guidance of any angle in a CT scanning plane, which can overcome an angle blind zone and greatly improve the practicality and compatibility of assistance in a puncture. A sequence and principle of the first translation mechanism 87 to perform a translation are as follows:

The third servo motor 86 drives the belt 871 to move through a received driving signal. The longer the driving signal, the longer the rotation time of the third servo motor 86 and thus the larger the displacement of the belt 871. Since the second translation mechanism 88 equipped with the guiding mechanism 89 is provided on the slide seat 872, the movement of the belt 871 will synchronously drive the guiding mechanism 89 to move. In this way, a distance for a puncture needle channel to be translated that is measured by a CT machine on an X-ray image is equal to a movement distance of the guiding mechanism 89, thereby allowing accurate guidance. In this embodiment, the belt 871 is a belt that is toothed at an inner side, which can prevent the belt 871 from undergoing a transmission error due to an insufficient tension force to reduce an accuracy. Of course, if conditions are met or a cost is not considered, the follower 873 can also be replaced by another servo motor running synchronously with the third servo motor 86, which can allow high consistency and stability. As another alternative structural design of this part, the belt can be driven by a chain and screw, and any change that needs to be made is merely intended to adapt to the second translation mechanism 88, for example, a size, a structure, a shape, and a material are set in various ways. However, no matter how a specific structure is changed, a technical effect allowed, a specific problem solved, and a working principle all are within or substantially the same as the first translation mechanism 87 disclosed in the present disclosure. Therefore, those skilled in the art can make any improvement according to the technical content of the present disclosure, and those skilled in the art can also seek additional technical enlightenment in a spatial multiaxial moving structure by enriching or changing a combination mode according to the technical basis provided in the present disclosure to allow multi-dimensional spatial positioning. In this embodiment, the combination of an in-plane one-dimensional linear movement by the first translation mechanism 87 with a two-dimensional plane movement by the second translation mechanism 88 can allow a dead space-free translation within a region of interest.

Figure 8:
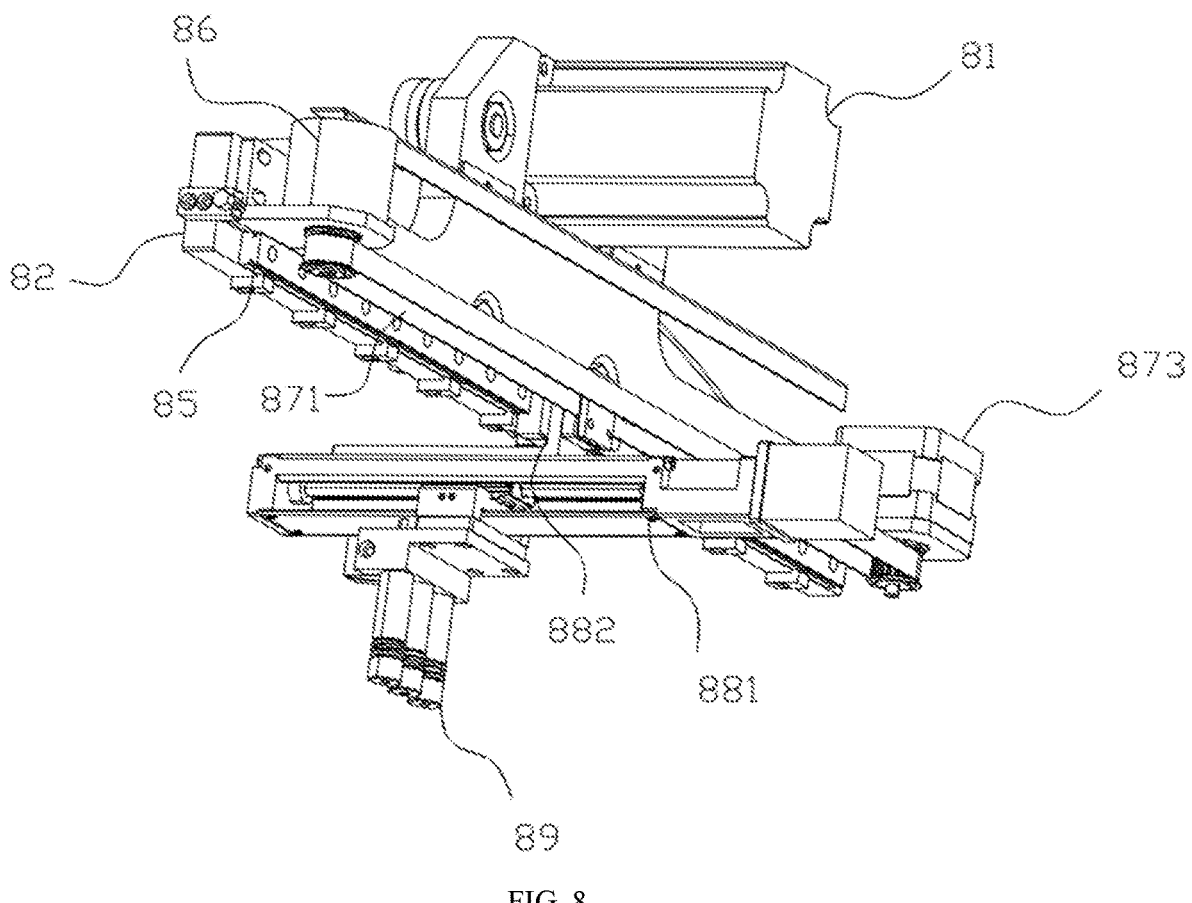
FIG. 8 is an axonometric view of a guiding apparatus.

In order to further illustrate a dead space-free guiding effect in a plane after the combination, the second translation mechanism 88 includes L-shaped bracket 882 fixedly connected to the slide seat 872; the L-shaped bracket 882 is removably connected to slide rail 881 arranged perpendicular to the second guide rail 85, and an end of the slide rail 881 is provided with a fourth servo motor; the fourth servo motor drives the guiding mechanism 89 to reciprocate along the slide rail 881 through a screw; and the guiding mechanism 89 includes one or more laser transmitters arranged along a same straight line. Specifically, as shown in FIG. 8, the second translation mechanism 88 is implemented by a screw structure. The first translation mechanism 87 and the second translation mechanism 88 in the present disclosure both can allow a one-dimensional linear adjustment, and can play a same role and exhibit a same technical effect. Therefore, without considering the space occupation and cost input, the first translation mechanism and the second translation mechanism can allow a same technical effect. In contrast, a cost of belt transmission is low, but the belt transmission requires a large structural space. The biggest advantage and ingenuity of belt transmission is that an adjustment can be conducted flexibly through the slide seat 872 and the belt 871. For example, the zero adjustment and error adjustment of initialization of the device can be allowed through a structural adjustment, and there is no need to change and debug all programs and devices in combination, which enables excellent compatibility.

Embodiment 4

On the basis of any of the above embodiments, as shown in FIG. 2, FIG. 3, FIG. 5, FIG. 7, and FIG. 9, the positioning apparatus further includes support arm 5 that has one end removably and fixedly connected to the first guide rail 7 and the other end rotatably connected to a head end of the support frame 2; and an end of the support arm 5 away from the first guide rail 7 is connected to the locking mechanism 4. A function of the locking mechanism 4 is to fix an angle between the support arm 5 and the support frame 2, such that the support arm 5 and the support frame 2 are always kept at preset relative angle positions to form a relative fixed structure before a position relationship between the two needs to be changed.

In order to allow the above technical effect and objective, more than one feasible technical solutions are provided in this embodiment, either of which is designed entirely according to the final technical effects of the present disclosure. Specifically, a manual locking mode and an automatic locking mode are adopted.

Figure 7:
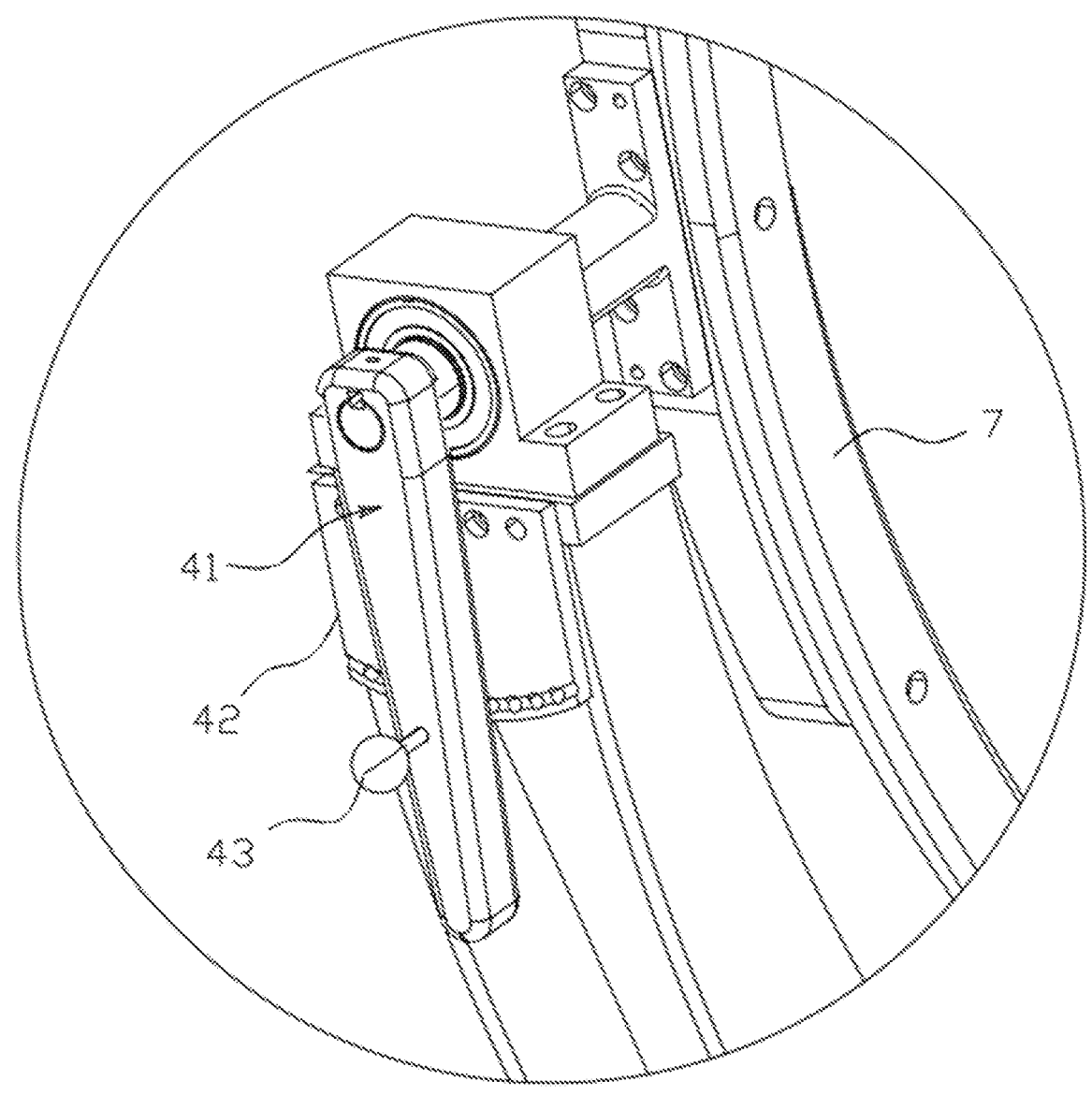
FIG. 7 is an enlarged view of C in FIG. 5.

As a structural design of the manual locking mechanism 4, as shown in FIG. 7, the locking mechanism 4 includes: a handle 41 fixedly connected to the support arm 5, where a locking pin 43 penetrates through the handle 41; and a locking plate 42 fixedly arranged on the support frame 2 and configured to cooperate with the locking pin 43 to lock the support arm 5, where the locking plate 42 is provided with a plurality of adjacent blind holes configured to accommodate the locking pin 43. When an adjustment is required, the locking pin 43 is pulled out, such that a free end of the locking pin 43 is separated from the blind hole on the locking plate 42, and thus the locking plate 42 does not limit and hinder the locking pin 43 in any way; then the handle 41 is rotated to make the support arm 5 rotate, thereby driving the first guide rail 7 to deflect; and when a preset deflection angle is reached, the locking pin 43 is inserted into a corresponding blind hole on the locking plate 42 to re-allow a locking state. The biggest advantage of this blind hole locking manner is high stability, and all locking structures are implemented by a full-mechanical structure. This blind hole locking manner is discrete locking, and has disadvantages such as non-linear locking angle. If linear locking is required, the blind hole locking manner needs to be replaced by a friction locking manner, but the friction locking manner requires a match angle instrument or an angle indicator to determine a deflection angle. The blind hole locking manner can allow the fixation of an angle through a blind hole of a preset fixed angle. If an angle interval between two adjacent or intersected blind holes is 1°, 2°, or 5° (which all are standard fixed values), then the selection of different blind holes is equivalent to fixation of a deflection angle. This locking mechanism is configured mainly most of deflection ranges in a head-foot direction. Because a deflection angle of deflection scanning of a CT machine is often small and the present application mainly matches a scanning application of a CT machine, a too-wide deflection angle range is not substantially useful. However, in an actual use, a deflection angle of a CT machine can be measured by the CT machine itself, and by keeping a deflection angle of the manual locking mechanism 4 consistent with a deflection angle of a CT machine, a deflection in a head-foot direction can remain consistent with a plane in which an X-ray image is located and thus can remain consistent with a direction of a preset puncture needle channel.

Figure 9:
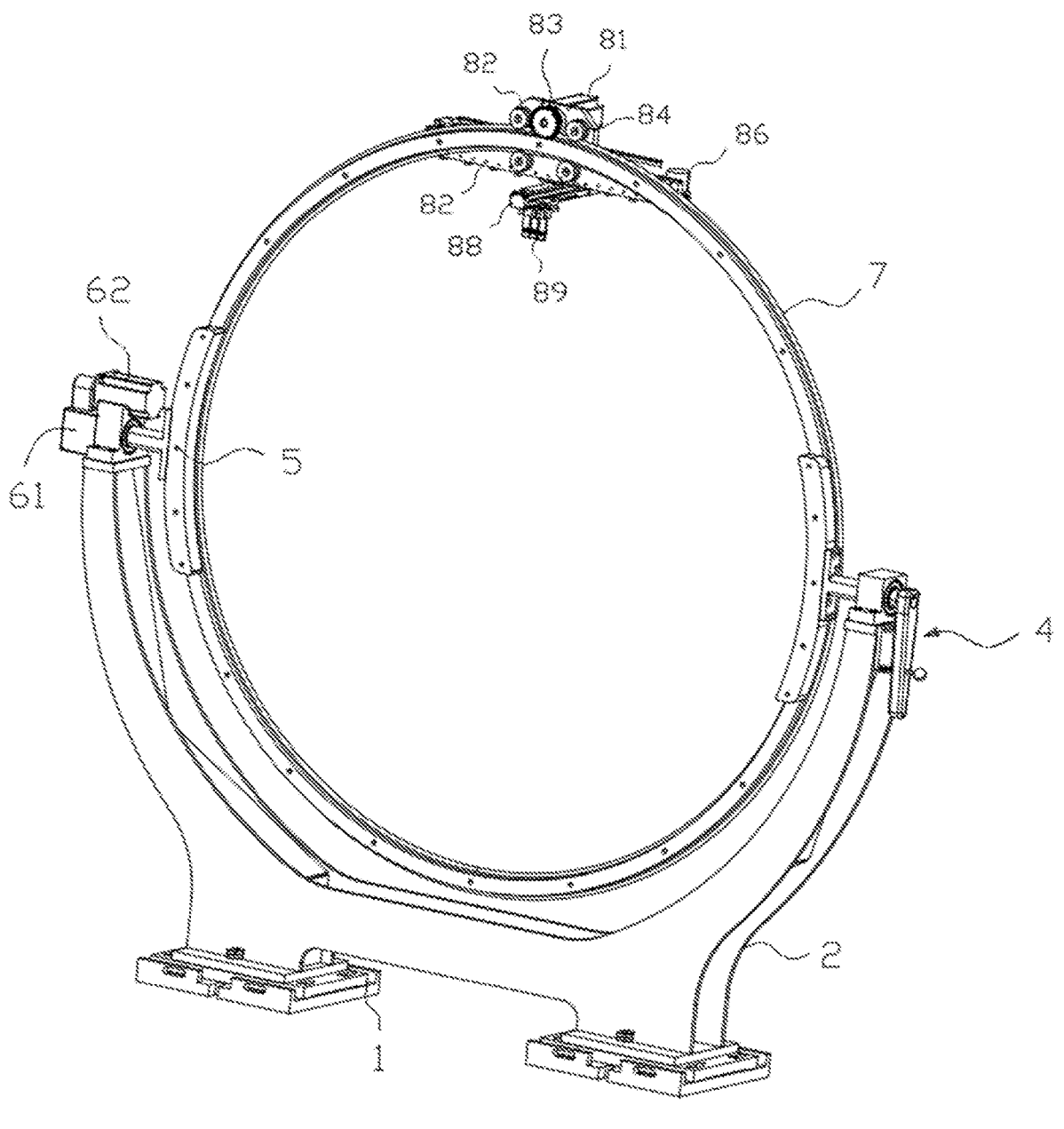
FIG. 9 is another visual axonometric view of the present disclosure.
Figure 10:
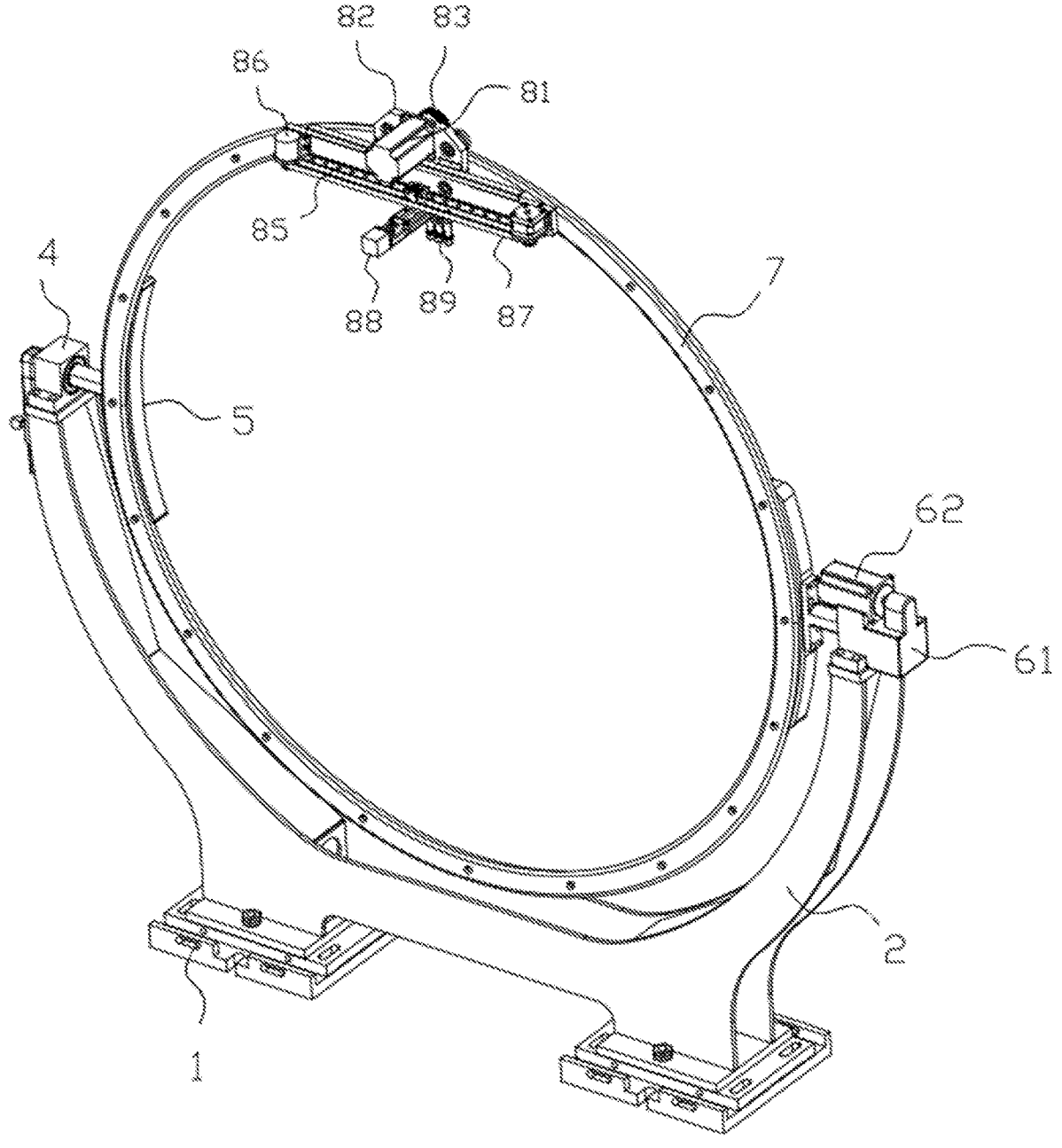
FIG. 10 is a reverse visual axonometric view of FIG. 9.

However, based on the limitations of the manual locking mechanism 4, an automatic locking structure is provided in this embodiment. As a structural design of a high-accuracy automatic locking mechanism 4, as shown in FIG. 9 and FIG. 10, the locking mechanism 4 includes reversing reducer 61 drivably connected to the support arm 5 and first servo motor 62 drivably connected to the reversing reducer 61. The driving of the servo motor can allow a linear control, solve an angle blind zone of manual locking, and lead to an accurate locking state; and the combination of the servo motor and the reversing reducer 61 can allow the support arm 5 to have large active deflection resistance and high stability, and can provide a flexible and suitable arrangement space according to an actual application scenario.

Embodiment 5

In order to acquire accurate and convenient control technical effects, the control part is mainly illustrated in this embodiment, and other principles and structural parts are described in detail in other embodiments. Specifically, the control mechanism includes the following units configured to acquire execution parameters: an input unit, including an ergonomic input module configured to acquire parameter information and/or a data analysis module configured to read imported message data;

a processing unit configured to allocate parameter information acquired by the input unit to a corresponding decoding module according to a preset control logic of a system, where the decoding module is configured to convert the parameter information into a corresponding driving signal; and an actuating unit configured to send a driving signal to the actuating mechanism according to a preset driving logic.

Figure 12:
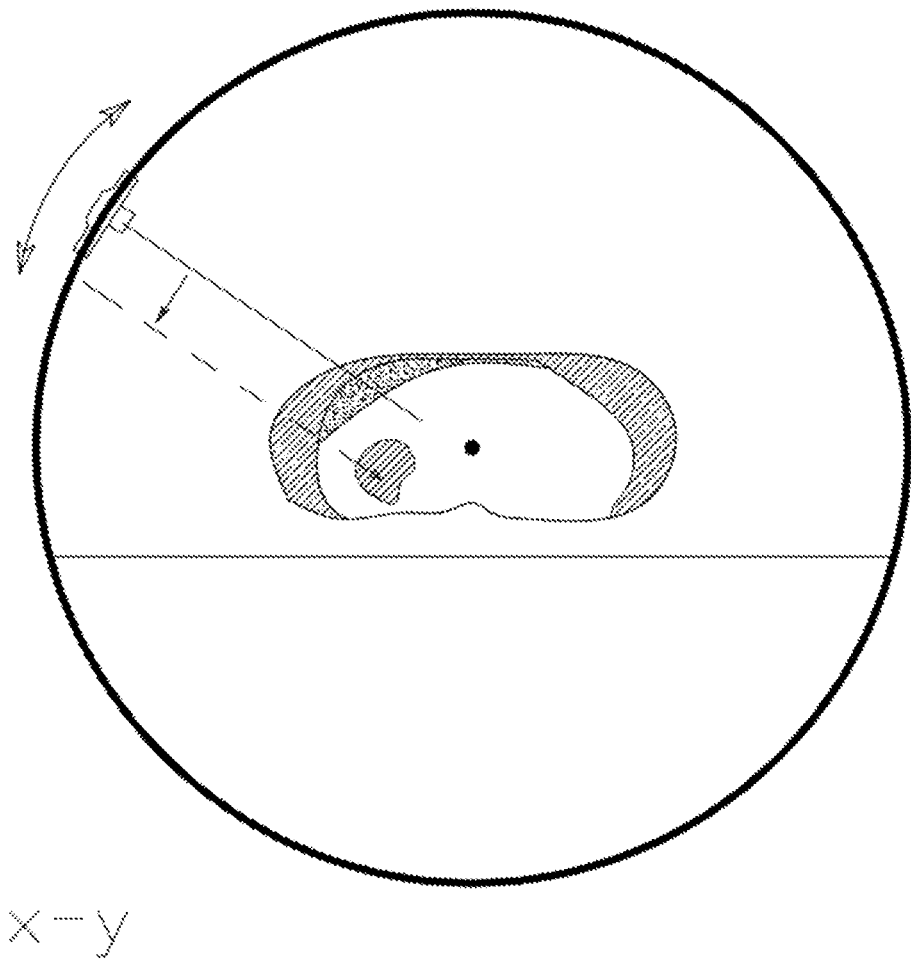
FIG. 12 is a schematic diagram of a guided deflection with FIG. 11 as a reference X-Y plane.
Figure 13:
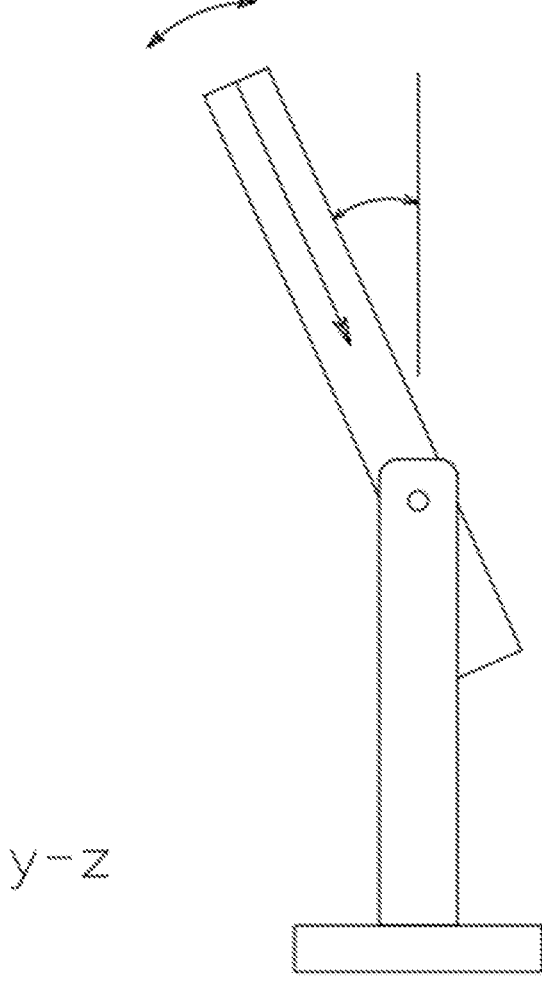
FIG. 13 is a schematic diagram of a guided deflection with FIG. 12 as a reference Y-Z plane.

The actuating mechanism involved in this embodiment involves the following operations: a deflection in a head-foot direction, where a corresponding execution hardware is the first servo motor 62, and the deflection is reflected as a rotation around an X axis in FIG. 11;

a movement in a head-foot direction, where a corresponding execution hardware is the fourth servo motor in the second translation mechanism 88, and the movement is reflected as a reciprocating translation along a Z axis shown in FIG. 11; and a translation in a radial plane of CT scanning at any angle, where a corresponding execution hardware is the second servo motor in the first translation mechanism 87, and the translation is reflected as a translation in the X-Y plane shown in FIG. 11. Specific conditions are shown in FIG. 12.

Embodiment 6

Accurate positioning is the basis and key point of the present disclosure, and the coaxial arrangement of the guiding and positioning device provided in the present disclosure and an inspection window of a CT machine is a premise and basis for accurate positioning. In order to allow the fast and efficient coaxial arrangement of the guiding and positioning device and an inspection window of a CT machine, it is necessary to constantly adjust the base 1 and support frame 2. In order to facilitate the adjustment and fixation, the base 1 is removably and fixedly connected to the support frame 2 through a connector; an adjustment mechanism in threaded connection with the support frame 2 is horizontally provided on the base 1; and the adjustment mechanism includes a first adjustment screw and a second adjustment screw, and projection lines of straight lines presented by the first adjustment screw and the second adjustment screw in a horizontal direction are perpendicular to each other. A linear fine adjustment can be conducted through the first adjustment screw and the second adjustment screw, and the two screws each can adjust 90°, such that a linear adjustment in any direction in a horizontal plane can be conducted through one or two of the two screws. When an adjustment is completed, the base 1 is fixedly connected to the support frame 2 to maintain a coaxial state of the guiding and positioning device and a CT machine. In a horizontal direction, a longitudinal adjustment is conducted through a preset foundation connected to the base 1, and then an adjustment result is verified by leveling instrument 3 arranged on the support frame 2, as shown in FIG. 5. The arrangement of the foundation is based on a CT machine that has been arranged and calibrated, and arranging and calibrating techniques are known in the prior art, which will not be repeated here.

In order to be compatible with a practical application scenario and a cost, preferably, a central angle corresponding to the first guide rail 7 is 180° to 360°. The larger the central angle of the first guide rail 7, the wider the available puncture range; and when the central angle of the first guide rail 7 reaches 360°, a dead space-free puncture can be allowed for a radial end face of a patient. A puncture is generally conducted from top to bottom, and if a puncture needs to be conducted from bottom to top, a patient needs to be in a lying posture. Therefore, the central angle of the first guide rail 7 generally does not need to be 360°, and extensive and comprehensive application scenarios involve a high probability of downward punctures and a small probability of horizontal punctures. Therefore, the arrangement of the first guide rail 7 at 270° can meet actual needs, and is conducive to the arrangement of the device, as shown by the front view of the device set at 270° in FIG. 1.

The above are merely preferred embodiments of the present disclosure, and are not intended to limit the present disclosure, and various modifications and changes may be made by a person skilled in the art to the present disclosure. Any modifications, equivalent substitutions, improvements, or the like made within the spirit and principle of the present disclosure shall fall within the protection scope of the present disclosure.

What is claimed is:

1. A guiding and positioning device for assisting in computed tomography-guided needle biopsy (CT-GNB), comprising: a control mechanism and an actuating mechanism, wherein the actuating mechanism comprises a base and a support frame arranged on the base to support a positioning apparatus;

the support frame has two head ends rotatably connected to the positioning apparatus, and one of the two head ends of the support frame is provided with a locking mechanism configured to limit a deflection angle of the positioning apparatus;

the positioning apparatus comprises a first guide rail in an arc shape, and the first guide rail is slidably provided with a guiding apparatus configured to guide a spatial puncture angle;

the guiding apparatus comprises a deflection drive mechanism slidable along the first guide rail, and a first translation mechanism and a second translation mechanism, wherein the first translation mechanism and the second translation mechanism are arranged perpendicular to each other;

the second translation mechanism is slidably provided with a guiding mechanism configured to guide a puncture through a visible laser space;

the deflection drive mechanism comprises a guide frame as a support body, a second servo motor removably and fixedly arranged on the guide frame, a driving wheel connected to the second servo motor and drivably connected to the first guide rail, and a plurality of stabilizing wheels rotatably arranged on the guide frame and located at inner and outer sides of the first guide rail; and the first translation mechanism comprises a second guide rail removably and fixedly arranged on the guide frame, a slide seat slidably clamped on the second guide rail, a third servo motor drivably connected to two ends of the second guide rail through a belt, and a follower; and the slide seat is removably and fixedly connected to the belt.

2. The guiding and positioning device according to claim 1, wherein the second translation mechanism comprises an L-shaped bracket fixedly connected to the slide seat; the L-shaped bracket is removably connected to a slide rail arranged perpendicular to the second guide rail, and an end of the slide rail is provided with a fourth servo motor; the fourth servo motor drives the guiding mechanism to reciprocate along the slide rail through a screw; and the guiding mechanism comprises at least one laser transmitter arranged along a same straight line.

3. The guiding and positioning device according to claim 1, wherein the control mechanism comprises the following units configured to acquire execution parameters:

an input unit, comprising an ergonomic input module configured to acquire parameter information and/or a data analysis module configured to read imported message data;

a processing unit configured to allocate the parameter information acquired by the input unit to a corresponding decoding module according to a preset control logic of a system, wherein the decoding module is configured to convert the parameter information into a corresponding driving signal; and an actuating unit configured to send a driving signal to the actuating mechanism according to a preset driving logic.

4. The guiding and positioning device according to claim 1, wherein a central angle corresponding to the first guide rail is 180° to 360°.

5. A guiding and positioning device for assisting in CT-GNB, comprising: a control mechanism and an actuating mechanism, wherein the actuating mechanism comprises a base and a support frame arranged on the base to support a positioning apparatus;

the support frame has two head ends rotatably connected to the positioning apparatus, and one of the two head ends of the support frame is provided with a locking mechanism configured to limit a deflection angle of the positioning apparatus;

the positioning apparatus comprises a first guide rail in an arc shape, and the first guide rail is slidably provided with a guiding apparatus configured to guide a spatial puncture angle;

the guiding apparatus comprises a deflection drive mechanism slidable along the first guide rail, and a first translation mechanism and a second translation mechanism, wherein the first translation mechanism and the second translation mechanism are arranged perpendicular to each other; and the second translation mechanism is slidably provided with a guiding mechanism configured to guide a puncture through a visible laser space;

wherein the positioning apparatus further comprises a support arm, wherein the support arm has a first end removably and fixedly connected to the first guide rail and a second end rotatably connected to a head end of the support frame; and an end of the support arm away from the first guide rail is connected to the locking mechanism.

6. The guiding and positioning device according to claim 5, wherein the locking mechanism comprises: a handle fixedly connected to the support arm, wherein a locking pin penetrates through the handle; and a locking plate fixedly arranged on the support frame and configured to cooperate with the locking pin to lock the support arm, wherein the locking plate is provided with a plurality of adjacent blind holes configured to accommodate the locking pin.

7. The guiding and positioning device according to claim 5, wherein the locking mechanism comprises a reversing reducer drivably connected to the support arm and a first servo motor drivably connected to the reversing reducer.

8. The guiding and positioning device according to claim 5, wherein the deflection drive mechanism comprises a guide frame as a support body, a second servo motor removably and fixedly arranged on the guide frame, a driving wheel connected to the second servo motor and drivably connected to the first guide rail, and a plurality of stabilizing wheels rotatably arranged on the guide frame and located at inner and outer sides of the first guide rail.

9. The guiding and positioning device according to claim 8, wherein the first translation mechanism comprises a second guide rail removably and fixedly arranged on the guide frame, a slide seat slidably clamped on the second guide rail, a third servo motor drivably connected to two ends of the second guide rail through a belt, and a follower; and the slide seat is removably and fixedly connected to the belt.

10. The guiding and positioning device according to claim 9, wherein the second translation mechanism comprises an L-shaped bracket fixedly connected to the slide seat; the L-shaped bracket is removably connected to a slide rail arranged perpendicular to the second guide rail, and an end of the slide rail is provided with a fourth servo motor; the fourth servo motor drives the guiding mechanism to reciprocate along the slide rail through a screw; and the guiding mechanism comprises at least one laser transmitter arranged along a same straight line.

11. A guiding and positioning device for assisting in CT-GNB, comprising: a control mechanism and an actuating mechanism, wherein the actuating mechanism comprises a base and a support frame arranged on the base to support a positioning apparatus;

the support frame has two head ends rotatably connected to the positioning apparatus, and one of the two head ends of the support frame is provided with a locking mechanism configured to limit a deflection angle of the positioning apparatus;

the positioning apparatus comprises a first guide rail in an arc shape, and the first guide rail is slidably provided with a guiding apparatus configured to guide a spatial puncture angle;

the guiding apparatus comprises a deflection drive mechanism slidable along the first guide rail, and a first translation mechanism and a second translation mechanism, wherein the first translation mechanism and the second translation mechanism are arranged perpendicular to each other;

the second translation mechanism is slidably provided with a guiding mechanism configured to guide a puncture through a visible laser space; and the base is removably and fixedly connected to the support frame through a connector; an adjustment mechanism in a threaded connection with the support frame is horizontally provided on the base; and the adjustment mechanism comprises a first adjustment screw and a second adjustment screw, and projection lines of straight lines presented by the first adjustment screw and the second adjustment screw in a horizontal direction are perpendicular to each other.

* * * * *